Figure 1:
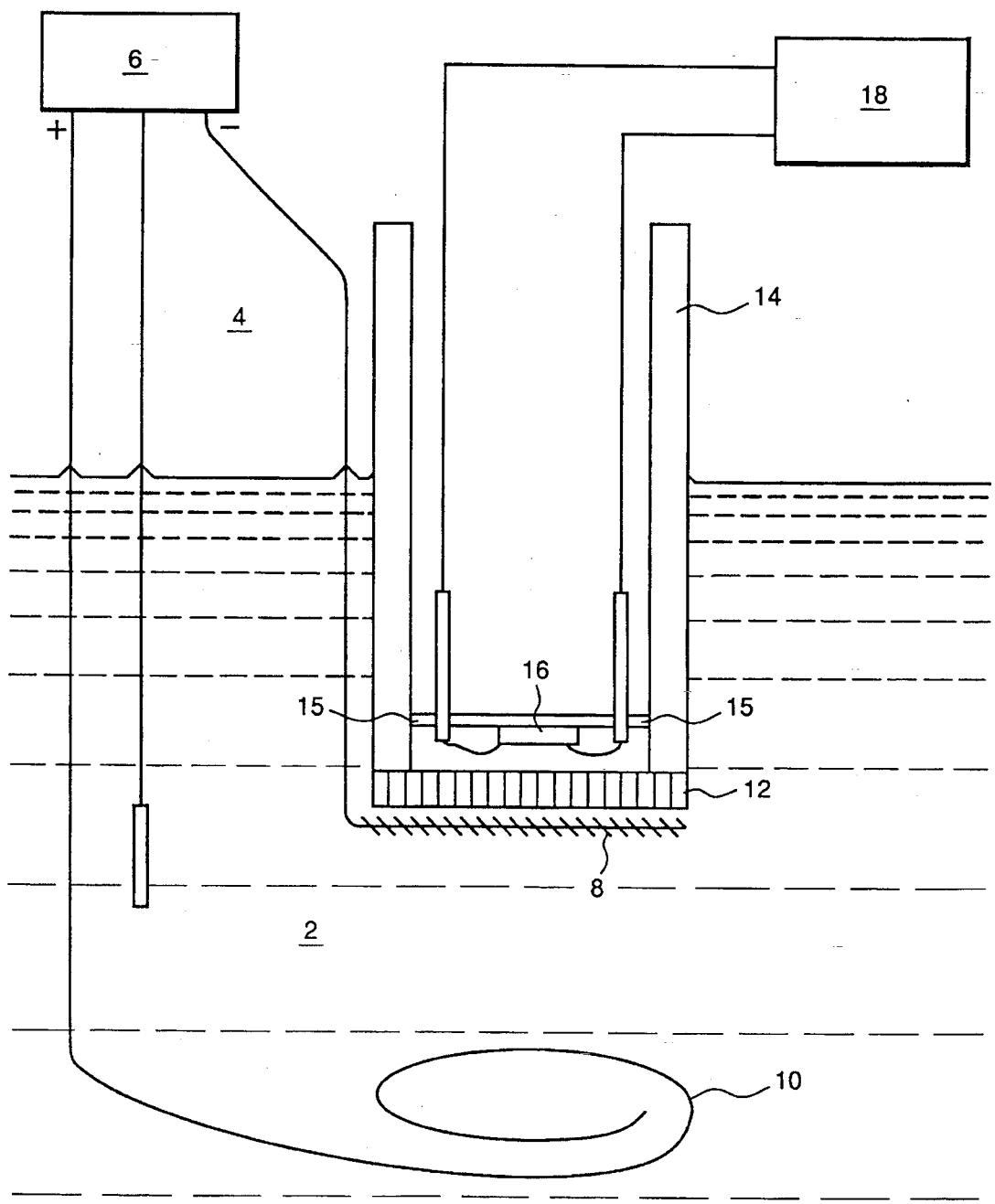

United States Patent [19]
Robins et al.

[11] Patent Number: 5,474,660
[45] Date of Patent: Dec. 12, 1995

[54] METHOD AND APPARATUS FOR DETERMINING THE CONCENTRATION OF AMMONIUM IONS IN SOLUTION

[75] Inventors: Ian Robins, Hillingdon; John E. A. Shaw, West Drayton, both of England

[73] Assignee: Central Research Laboratories Limited, Middlesex, United Kingdom

[21] Appl. No.: 295,645

[22] PCT Filed: Apr. 1, 1993

[86] PCT No.: PCT/GB93/00680

§ 371 Date: Aug. 26, 1994

§ 102(e) Date: Aug. 26, 1994

[87] PCT Pub. No.: WO93/22668

PCT Pub. Date: Nov. 11, 1993

[30] Foreign Application Priority Data

Apr. 23, 1992 [GB] United Kingdom ................... 9208780

[51] Int. Cl.$^6$ ................................................ G01N 27/26
[52] U.S. Cl. ....................... 204/153.14; 204/153.1; 204/400; 204/415; 257/414
[58] Field of Search ......................... 204/153.17, 153.14, 204/153.1, 129, 400, 415; 257/414

[56] References Cited

U.S. PATENT DOCUMENTS

| | | | |
|---|---|---|---|
| 3,003,932 | 10/1961 | Frey et al. | 204/431 |
| 3,367,850 | 2/1968 | Johnson | 204/153.22 |
| 3,649,505 | 3/1972 | Strickler et al. | 204/153.14 |
| 4,081,345 | 3/1978 | Tolg et al. | 204/153.14 |
| 4,152,215 | 5/1979 | Yoshino et al. | 204/301 |
| 4,267,023 | 5/1981 | Frant et al. | 204/153.14 |
| 4,289,299 | 6/1980 | Carlson | 204/153.14 |
| 4,451,347 | 5/1984 | Wullenweber | 204/129 |
| 4,650,561 | 3/1987 | Robins et al. | 204/153.14 |

FOREIGN PATENT DOCUMENTS

92/15877 9/1992 WIPO .

Primary Examiner—T. Tung
Attorney, Agent, or Firm—Keck, Mahin & Cate

[57] ABSTRACT

An ammonia gas sensor 16 is housed within a container 14 partially immersed in a solution 2 containing ammonium ions. An electrochemical generator 6, 8, 10 generates hydroxyl ions in a region of the solution 2 adjacent the container 14. This converts ammonium ions to ammonia gas which is sensed by the sensor 16 having passed through a gas-permeable member 12. This sensing provides an indication of the concentration of ammonium ions in the solution 2.

11 Claims, 2 Drawing Sheets

METHOD AND APPARATUS FOR DETERMINING THE CONCENTRATION OF AMMONIUM IONS IN SOLUTION

The present invention relates to a method and apparatus for determining the concentration of ammonium ions in solution and has particular, although not exclusive, applicability to analysis of aqueous solutions such as contaminated water supplies and bodily fluids where ammonium ions may be produced by enzymatic action as for urea in blood.

Techniques for sensing the concentration of ammonia in a gas phase, and in a gas phase above and in equilibrium with a solution containing dissolved ammonia are known. Such techniques may then be used to determine the concentration of ammonium ions in the solution by utilising the pH-dependent relationship which exists between the concentration of ammonium ions and ammonia in solution and the relationship which exists between ammonia gas and dissolved ammonia in equilibrium at the gas/liquid interface. It is known that by increasing the alkalinity of a solution containing ammonium ions, then ammonia may be generated within the solution. Increasing the alkalinity of such a solution may most conveniently be achieved by adding to the solution either alkali or buffer reagents such as sodium hydroxide or potassium hydroxide as disclosed in EP-A-359158. However, addition of such reagents to the solution may be undesirable because the use of consumables is inconvenient and may also cause unwanted hydrolysis of biochemical materials leading to an increase in ammonium ion and ammonia levels.

Alternatively, the concentration of ammonium ions in solution may themselves be directly sensed by, for example, using an ammonium ion sensitive device within the solution.

Both the above known techniques suffer from various shortcomings. The former, for example, because of the addition of alkali or buffer reagents. The latter, for example, because an ion sensitive device in the solution will have at least a degree of cross-sensitivity to $Na^+$ or $K^+$ ions as well as being predominantly sensitive to $NH_4^+$ ions. Similarly $Na^+$ and $K^+$ ion sensitive electrodes show a degree of cross-sensitivity to $NH_4^+$ ions. As a result of the mutual cross-sensitivity of these ion sensitive devices, an analysis based upon a combination of such electrodes may be unsatisfactory, especially for an ion only present at low concentrations.

It is thus an object of the present invention to at least alleviate the aforementioned shortcomings by avoiding the need to add alkali or buffer reagents to the solution under test and also to avoid the need to sense the ion concentration in the solution itself.

Hence a first aspect of the present invention provides a method of determining the concentration of ammonium ions in solution, comprising:

electrochemically generating hydroxyl ions within the solution to render at least a portion of the solution alkaline thereby to convert ammonium ions to ammonia;

allowing the said ammonia to pass through a gas-permeable member into a region remote from the solution; and sensing the concentration of ammonia gas in the region, which concentration is representative of the concentration of ammonium ions in the solution. Thus there need be no contaminants added to the solution and also a sensor can be used which is not generally prone to cross-sensitivity to cations other than ammonium ions in the solution.

Preferably the electrochemical generation of hydroxyl ions occurs adjacent to the gas-permeable member. This is because the ammonia in the gas phase arises through a partition between the gas phase and that part of the solution which is adjacent the gas phase, which boundary is formed at the gas-permeable member. Adjustment of the pH of only a restricted region close to the gas-permeable member limits the quantity of electrochemically generated hydroxyl ions required and hence reduces the charge which needs to be passed through electrodes employed in the generation.

Advantageously the gas-permeable member is a membrane structure.

Preferably, sensing of the ammonia is achieved by employing an ammonia gas sensor device such as a gas-sensitive field effect transistor device.

A second aspect of the present invention provides apparatus for the determination of the concentration of ammonium ions in solution, comprising:

an electrochemical generator for generating hydroxyl ions in the solution to render the solution alkaline thereby to convert ammonium ions to ammonia;

a gas-permeable member for permitting the passage of the said ammonia therethrough into a region remote from the solution; and an ammonia gas sensor device for sensing the concentration of ammonia gas in the region, which concentration is representative of the concentration of ammonium ions in the solution. Preferably the electrochemical generator is an electrode structure.

Figure 2:
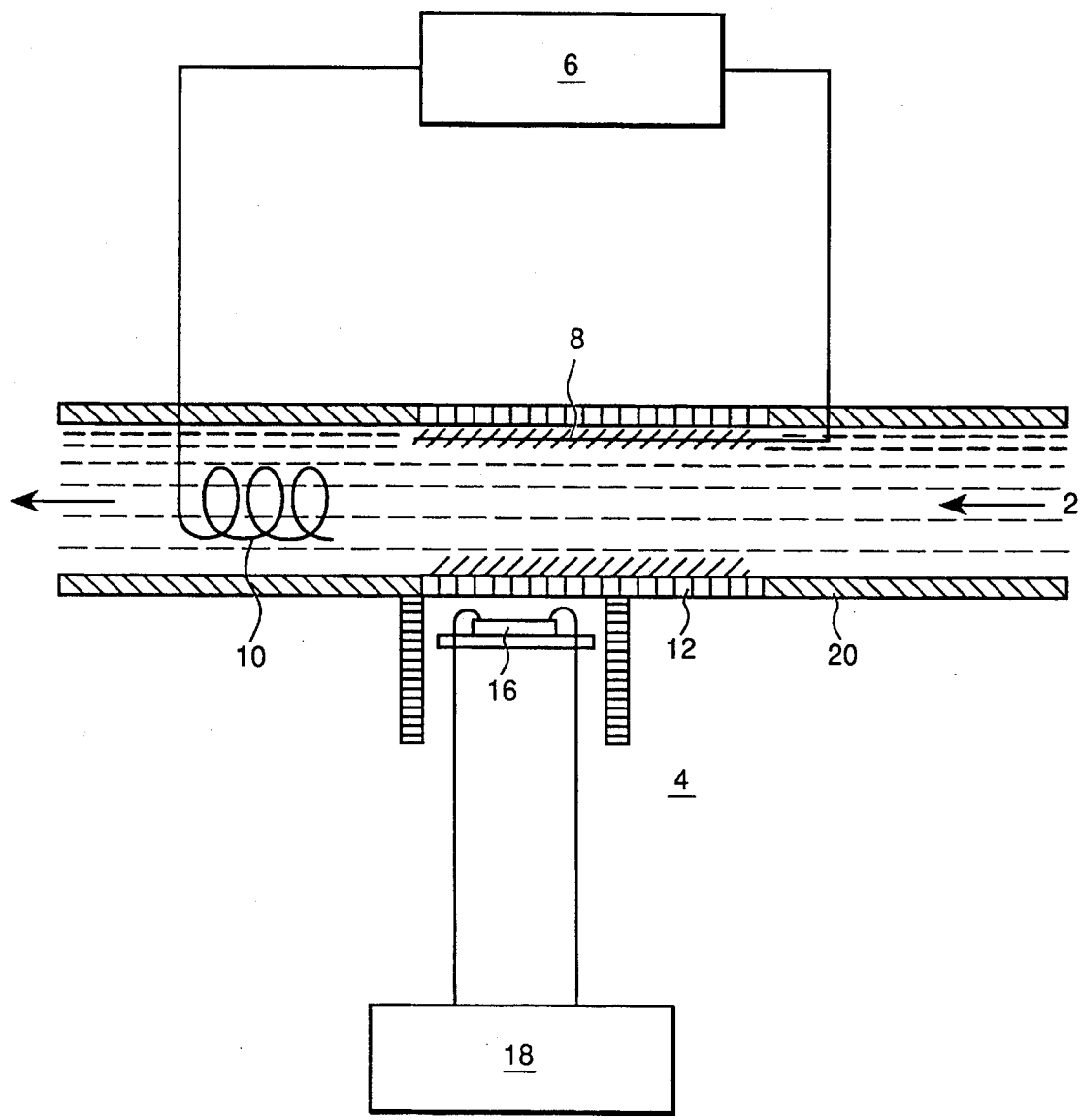

The invention will now be described, by way of example only, with reference to the accompanying drawings of which:

FIG. 1 is a schematic illustration of an apparatus in accordance with the invention; and FIG. 2 is a schematic illustration of an alternative apparatus.

Referring firstly to FIG. 1, it will be seen that a solution 2 under test includes water with ammonia dissolved therein. It will be understood that the ammonium ion concentration and the concentration of dissolved ammonia in the solution are directly linked by the reaction:

$$NH_3 + H_2O \rightarrow NH_4^+ + OH^-$$

This reaction has an equilibrium constant, $K_b$, given by:

$$K_b = \frac{[NH_4^+][OH^-]}{[NH_3(aq)]}$$

The ammonium ion concentration may be related to the concentration of dissolved ammonia in the solution by a knowledge of both the value of $K_b$ and the pH of the solution.

Furthermore, the partition of ammonia between the air 4 above and in close proximity to the sample solution 2 adjacent the region where the ammonia is generated within solution 2 is related by:

$$[NH_3(aq)] = C[NH_3(g)]$$

where C is the partition coefficient.

Hence, when the concentration of ammonia in the air 4 is in equilibrium with that contained within solution 2, then this concentration is directly related to the concentration of ammonium ions in the solution 2 by:

$$[NH_4^+] = \frac{K_b[NH_3(aq)]}{[OH^-]}$$

$$= \frac{K_b C[NH_3(g)]}{[OH^-]}$$

$$= \frac{K_b C[NH_3(g)]}{10^{-(pK_w - pH)}}$$

Where $K_w$ is the ionisation constant of water.

Published data exists for the equilibrium concentrations of ammonia in aqueous solutions and in the gas phase over a range of temperatures and from this data values for the partition coefficient, C, may be readily obtained. Similarly, published data extending over a range of temperatures exists for the ammonia dissociation constant, $K_b$, and ionisation constant for water, $K_w$.

Methods of measuring the pH and temperature values, although necessary, are not germane to the present invention and so will not be discussed herein. Those skilled in the art will realise how such measurements may be performed.

From a consideration of the above, it will be apparent that as the pH of the solution 2 increases in alkalinity, then so does the fraction of ammonia dissolved in the solution 2 and hence the concentration of aqueous ammonia. The values of $K_b$ are such that for pH values of 12 or more, the dissolved ammonium ions in solution 2 may be considered to be completely converted to aqueous ammonia.

Increasing the alkalinity of a portion of the solution 2 is achieved by utilising an electrochemical generator such as an electrical circuit 6 comprising a porous conductive hydroxyl ion generating electrode 8 and counter electrode 10. In the present example, circuit 6 provides an emf across the electrodes 8,10 such that conventional current flows in the direction 6 to 10 and reduction of oxygen in the aqueous solution 2 at electrode 8 produces hydroxyl ions according to the following reaction:

$$O_2 + 2H_2O + 4e^- \rightarrow 4OH^-$$

Because of the local increase in pH around the electrode 8, ammonia gas will be generated, as detailed above. This ammonia gas is allowed to pass through a gas-permeable member such as membrane structure 12, because ammonia gas sensor devices cannot directly contact the solution 2. Membrane 12 may advantageously be formed from a microporous organic polymer material, for example, PTFE, polypropylene or polyethylene.

In this example, the membrane 12 is held in close proximity to and adjacent electrode 8 such that ammonia gas may easily permeate the membrane 12. Such a close relationship is not, however, imperative, yet is desirable in order to minimise the quantity of current required.

On travelling through the membrane 12, the ammonia gas enters a container 14. In container 14 is housed an ammonia gas sensor device such as catalytic metal gate field effect transistor 16. A barrier 15 which may form part of the transistor 16 housing, is positioned in container 14 so as to largely, but not necessarily completely, restrict exchange of gas between the transistor 16 region close to the membrane 12 and the remainder of the container 14 and the open atmosphere therebeyond. This restriction prevents excessively rapid loss of ammonia gas and this allows the confined region to remain in equilibrium with the solution 2 beyond the membrane 12, while oxygen, present at a much higher concentration, may pass through to the membrane 12 and the electrode 8 in solution 2 to support the hydroxyl-producing electrochemical reaction. Transistor 16 is connected to a sensor and readout circuit, shown generally as 18. Circuit 18, which is not germane to the present invention, is capable of providing an output representative of the concentration of ammonia gas in the air 4. Because this ammonia gas will be generated predominantly by the hydroxyl ions creating an alkaline region of the solution 2 adjacent the membrane 12, then by virtue of the above this concentration may be directly related, as given by the reactions above, to the concentration of ammonium ions in the solution 2.

In the above example, illustrated in FIG. 1, not only is the membrane 12 effective to allow ammonia gas to pass into container 14 to be sensed, but is also effective to allow oxygen to pass from the air 4 into the solution 2. This is necessary in order to allow hydroxyl generation by electrochemical reaction:

$$O_2 + 2H_2O + 4e^- \rightarrow 4OH^-$$

The only requirements placed on the gas permeable member, exemplified by membrane 12, are that it be permeable to gas, yet impervious to ion migration or fluid flow.

An alternative embodiment of the present invention is illustrated in FIG. 2. In this figure, like components are numbered to correspond to those of FIG. 1.

In the embodiment of FIG. 2, it will be seen that solution 2 flows through a channel 20 and is then subject to the same method as described above. Such an embodiment may usefully be employed when the solution under test is, for example, blood and the species to be determined is ammonium ion or materials yielding ammonium ion by enzymatic action, e.g. urea.

It will be apparent that when current is passed between electrodes 8 and 10, the increase in pH is greatest in the region adjacent the electrode 8. Preferably the current is adjusted to a level generating sufficient hydroxyl ions adjacent the membrane 12 to convert essentially all the ammonium ions in that region to ammonia. This condition will maximise the signal produced by the transistor 16 in response to ammonia gas and may be recognised by this maximisation of response. This condition corresponds to a pH of 12 or greater adjacent the membrane 12, but it is not necessary to measure pH in this region. From the signal produced by transistor 16, a measurement of solution 2 temperature and a corresponding value for the partition coefficient, C, form the available published data, a calculation may be made of the concentration of dissolved ammonia in the solution 2 adjacent membrane 12 by using the expression:

$$[NH_3(aq)] = C[NH_3(g)]$$

The dissolved ammonia in the solution 2 in the region adjacent membrane 12 will equate to the total ammonium ion and ammonia concentrations in the bulk solution 2 expressed in molar or molal terms. Where the concentration of ammonium ions in the bulk solution 2 is desired to be known, this is calculated using a measurement of the bulk solution 2 pH (remote from electrodes 8, 10 or prior to passing a current therethrough), and temperature in combination with published data values for $K_b$ and $K_w$ using the expression:

$$[NH_4^+] = \frac{K_b[NH_3(aq)]}{10^{-(pKw-pH)}}$$

Alternatively, by still employing temperature and pH measurements, the circuit 6, electrodes 8, 10 and transistor 16 may be calibrated using a ammonium ion solution of known concentration. This may allow for some deviation from equilibrium conditions and mass transport effects.

In the examples described herebefore, the electrode 8 is chosen to be a planar porous structure. With this arrangement a "layer" of hydroxyl ions will be formed around the electrode 8. The greater the quantity of charge passed through electrodes 8, 10 (i.e. current), then the greater the quantity of hydroxyl ions produced and and this will alter the pH of the bulk solution 2. In principle only a small volume of solution 2 adjacent the electrode 8 needs to be charged, but if this volume is too small, then the quantity of ammonia diffusing out into the bulk solution and also through membrane 12 will cause the concentration of ammonia in the portion of the solution 2 adjacent the membrane 12 to drop and hence produce erroneous measurements.

Furthermore the geometry of the electrode 8 as well as the geometry of the membrane 12 and transistor 16 will have a bearing in the overall performance of the apparatus by affecting the quantity of charge which needs to be developed by application of the emf in order to generate the hydroxyl "layer" and also the degree to which equilibrium conditions may be approached.

It will be appreciated by those skilled in the art that in the above example when reference is made to the air 4 above the solution 2, this is a small volume of the air directly above and adjacent the membrane 12. The reason for this is that only in such a close proximity to the place where ammonia is generated from the solution may highly accurate measurements of ammonia concentration be made.

Thus has been described a method and apparatus for determining the concentration of ammonium ions in solution which is substantially immune to interferences from ions such as Na$^+$ and K$^+$.

It will be appreciated that although the production of hydroxyl ions occur, in the above example, in a region adjacent the membrane 12, this is not imperative. Hydroxyl ions may be generated in any region of the solution 2, or indeed throughout the whole of solution 2.

We claim:

1. Apparatus for determining the concentration of ammonium ions in a solution, comprising:

a gas permeable member defining a barrier between the solution of ammonium ions and a region remote from the solution, the remote region having a gaseous environment, an ammonia gas sensing device disposed in the remote region gaseous environment, an electrochemical generator for generating hydroxyl ions in the solution, the generator including an electrode disposed in the solution adjacent to the gas permeable member to define a local hydroxyl ion forming region adjacent the gas permeable member, whereby in operation hydroxyl ions are produced in the local hydroxyl ion forming region by reduction of oxygen gas which passes from the remote region through the gas permeable member into the hydroxyl ion forming region in order to permit, by reaction between hydroxyl ions and ammonium ions the creation of ammonia, a proportion of which transfers as ammonia gas into the remote region through the gas permeable member for sensing by said ammonia gas sensing device, concentration of ammonia gas being proportionally representative of the concentration of ammonium ions in the solution.

2. Apparatus according to claim 1, wherein the gas permeable member is a microporous organic polymer membrane.

3. Apparatus according to claim 1, wherein the ammonia gas sensing device is positioned close to the gas permeable member, and comprises barrier means to prevent rapid convective loss of ammonia gas from a region of the ammonia gas sensing device, while allowing ingress of oxygen to and through the gas permeable member to the solution.

4. Apparatus according to claim 1, wherein the ammonia gas sensing device comprises a catalytic metal gate field effect transistor.

5. Apparatus according to claim 1, comprising a container, a wall of the container including said gas permeable member, and the ammonia gas sensing device being mounted in the container.

6. Apparatus according to claim 1, comprising a conduit for the solution, the conduit having a wall in which the gas permeable member is formed.

7. Apparatus according to claim 1, wherein the electrode is a porous planar electrode disposed adjacent the gas permeable member.

8. A method for determining the concentration of ammonium ions in a solution including:

(1) providing a gas permeable member defining a barrier between the solution of ammonium ions and a gaseous environment region remote from the solution;

(2) electrochemically generating hydroxyl ions in a hydroxyl ion forming region adjacent the gas permeable member, the size of the hydroxyl ion forming region being small in relation to a volume occupied by the solution;

(3) allowing oxygen gas to pass from the remote region through the gas permeable membrane to the hydroxyl ion forming region, and allowing ammonia gas generated within the hydroxyl ion forming region to pass through the gas permeable member into the remote region; and (4) sensing the concentration of ammonia gas in the remote region gaseous environment, which concentration is a proportional representation of the concentration of ammonium ions in the solution.

9. A method according to claim 8, comprising providing an electrode adjacent to the gas permeable membrane within the solution for generating hydroxyl ions.

10. A method according to claim 7, comprising restricting the flow of ammonia gas in the remote region mainly to an area adjacent the gas permeable member, where said sensing takes place.

11. A method for determining the concentration of ammonium ions in solution comprising:

(1) providing a solution of ammonium ions, providing a region having a gaseous environment remote from the solution, and providing a gas permeable member defining a barrier between the remote region and the solution;

(2) allowing oxygen gas to pass from the remote region through the gas permeable member, and electrochemically generating hydroxyl ions within the solution adjacent to the gas permeable member in order to establish reactions within the solution adjacent to the gas permeable member which result in the formation of ammonia, (3) allowing the ammonia to pass as a gas through the gas permeable member into the remote region, and sensing the concentration of ammonia gas in the remote region gaseous environment to provide a signal representative of the concentration of ammonium ions in the solution.

* * * * *